(12) United States Patent
Hallstadius et al.

(10) Patent No.: US 7,246,530 B2
(45) Date of Patent: Jul. 24, 2007

(54) FLOW SENSOR AND METHOD FOR MEASURING A FLOW RATE COMPONENT OF A FLUID CONTAINING ELECTRICALLY CHARGED ELEMENTS

(75) Inventors: Hans Hallstadius, Lund (SE); Göran Ohlsson, Örkelljunga (SE); Sven Gustafson, Lund (SE); Bengt Jonasson, Hörby (SE); Gert-Inge Bertinsson, Lund (SE)

(73) Assignee: Gambro Lundia AB, Lund (SE)

( * ) Notice: Subject to any disclaimer, the term of this patent is extended or adjusted under 35 U.S.C. 154(b) by 212 days.

(21) Appl. No.: 10/544,671

(22) PCT Filed: Jan. 26, 2004

(86) PCT No.: PCT/SE2004/000097

§ 371 (c)(1),
(2), (4) Date: Aug. 4, 2005

(87) PCT Pub. No.: WO2004/070323

PCT Pub. Date: Aug. 19, 2004

(65) Prior Publication Data

US 2006/0096389 A1    May 11, 2006

Related U.S. Application Data

(60) Provisional application No. 60/523,723, filed on Nov. 19, 2003.

(30) Foreign Application Priority Data

Feb. 10, 2003   (SE) .................................... 0300342

(51) Int. Cl.
*G01F 1/56* (2006.01)
(52) U.S. Cl. ................................................ 73/861.08

(58) Field of Classification Search ....... 73/861.12–16, 73/861.08
See application file for complete search history.

(56) References Cited

U.S. PATENT DOCUMENTS 4,612,806 A * 9/1986 Feller .......................... 73/195
4,616,509 A * 10/1986 Feller ...................... 73/861.05
5,392,657 A * 2/1995 Feller ...................... 73/861.77

(Continued)

FOREIGN PATENT DOCUMENTS

JP          60-237321          11/1985

*Primary Examiner*—Jewel Thompson
(74) *Attorney, Agent, or Firm*—Finnegan, Henderson, Farabow, Garrett & Dunner, L.L.P.

(57) ABSTRACT

The invention relates to measurement of a fluid flow, wherein a flow rate component of the fluid is measured along a selected direction. A magnetic field whose polarity varies over time is applied to the fluid, which presumed to contain electrically charged elements. First and second sensor electrodes (120, 121) are arranged to be wetted by the flowing fluid. The electrodes (120, 121) are spaced apart from one another along a line being substantially perpendicular both to the selected flow direction and a magnetic axis of the magnetic field. A DC-level drift of the sensor electrodes (120, 121) is prevented by supplying a control current ($I_{ctrl-0}$; $I_{ctrl-1}$) to each of the sensor electrode (120, 121), which has such sign and magnitude that a direct-current voltage level at the sensor electrodes (120, 121) relative areference potential is controled towards a predetermined voltage ($DC_{set}$).

14 Claims, 3 Drawing Sheets

U.S. PATENT DOCUMENTS

| | | |
|---|---|---|
| 6,431,011 B1 | 8/2002 | Feller |
| 2002/0050175 A1 | 5/2002 | Feller |
| 2002/0145417 A1 | 10/2002 | Brockhaus |
| 2003/0005777 A1 | 1/2003 | Budmiger |

* cited by examiner

FLOW SENSOR AND METHOD FOR MEASURING A FLOW RATE COMPONENT OF A FLUID CONTAINING ELECTRICALLY CHARGED ELEMENTS

CROSS REFERENCE TO RELATED APPLICATIONS

This application is an national phase application based on POT/SE2004/1000097, filed Jan. 26, 2004, which claims the priority of Sweden Application No. 0300342-3, filed Feb. 10, 2003, and the benefit of U.S. Provisional Application No. 60/523,723, filed Nov. 19, 2003, the content of each of which is incorporated herein by reference in its entirety.

THE BACKGROUND OF THE INVENTION AND PRIOR ART

The present invention relates generally to measurement of a fluid flow. More particularly the invention relates to a flow sensor according to the preamble of claim 1, an ultra-filtration measuring unit according to the preamble of claim 8 and a method for measuring a flow rate component according to the preamble of claim 10.

There are many technical areas in which an accurate fluid flow measurement is required. Numerous representative applications can, for instance be found in the field of medical technology. However, some kind of flow measurement is normally required in most instances where a fluid/liquid is to be transported from one point to another. Fluid flow measurements may also be used to determine the velocity of a craft traveling in water or a similar liquid. Naturally, mechanical flow sensors may here be employed. Nevertheless, when a high accuracy is required, electromagnetic flow measurement sensors are generally preferable. This type of sensors are based on a well-known technique where a magnetic field is applied to interact with electrically charged elements, such as ions, in the flowing fluid to produce a resulting electric field. Thus, according to Faraday's law, the magnitude of the induced electric field constitutes a measure of the flow rate of the fluid.

The applicant develops and manufactures medical equipment, for instance renal products in the form of dialysis apparatuses, which utilize such an electromagnetic flow measurement technique. Commonly, flow sensors with platinum electrodes have been employed to deliver accurate and reliable values of the registered fluid flows. Platinum, and platinum black in particular, namely accomplishes a good electrical contact between the electrodes and the dialysis liquid, so that the electrode dimensions can be held comparatively small, and consequently give rise to a linear magnetic field pattern in the fluid conduit cross section.

In recent years, a so-called glucose-charging practice has been introduced wherein glucose is added to the dialysis liquid in order to better imitate the composition of the patient's own blood, and thereby i.a. avoid certain metabolic risks for the patient. However, glucose also produces undesired effects due to its electrochemical activity with platinum. During operation of a dialysis apparatus with a glucose-charged dialysis liquid, a catalytic reaction causes glucose to be oxidized on the flow sensors' platinum surfaces. This decreases the reliability of the flow measurements. Namely, the oxidation may result in a varying DC-level (DC=Direct Current) at the sensor electrodes, which in turn renders it difficult to determine the contribution to the registered electric field caused by the electromagnetic interaction between the applied magnetic field and the charged elements in the flowing liquid (i.e. here ions in the dialysis liquid).

The U.S. Patent Application No. 2002/0050175 describes a magnetic flow sensor and method, wherein an undesired drift of the electrode voltages is compensated for, either by interconnecting the sensing electrodes or by connecting them to a common potential, such as ground. Also in this case, a voltage indicative of the flow rate is measured by means of at least two electrodes. A high-impedance voltage-measurement circuit is used to register a voltage between the electrodes. Thus, during the measurement, the electrodes are in an open circuit state, and may therefore be electrically influenced by electrode polarization and other measurement error-inducing factors that develop relatively slowly. In order to avoid such effects, the electrodes are in a closed circuit state for most of the time and placed in an open circuit state only during a relatively brief measurement interval portion of the operating cycle.

Although this strategy may solve the drifting problem, it results in a limited maximum sampling frequency, and consequently also an accuracy constraint with respect to the detection of rapid changes in the flow rate. Moreover, the procedure requires a considerable amount of high-speed switching, and is therefore both expensive to implement and relatively prone to malfunction.

SUMMARY OF THE INVENTION

The object of the present invention is therefore to alleviate the problems above and thus accomplish a flow measurement solution through which an accurate fluid flow rate can be determined also when the sensor electrodes may be electrochemically affected by the fluid and its constituents.

According to one aspect of the invention, the object is achieved by the initially described flow sensor, which is characterized in that it comprises at least one direct current supply circuit adapted to feed a respective control current to each of the first and second sensor electrodes in the electric sensor arrangement. Each control currents has such sign and magnitude that a DC-voltage level at the first and second sensor electrodes relative to a reference potential is controlled towards a predetermined voltage.

An important advantage attained by this strategy is that any DC-level drift which otherwise could have occurred due to an oxidation of one or more of the sensor electrodes is prevented. At the same time, the flow measurement may be performed continuously, and/or flow rate sample values may be generated at an arbitrary frequency.

According to a preferred embodiment of this aspect of the invention, the at least one direct current supply circuit includes a differential low-pass filtering unit, an integrator unit and a controllable current generator. The differential low-pass filtering unit is adapted to generate a low-pass filtered difference signal representing a variance between the predetermined voltage and the registered voltage. The integrator unit is adapted to receive the low-pass filtered difference signal, and in response thereto, produce an adjustment signal. Finally, the controllable current generator is adapted to produce the control current in response to the adjustment signal. This design of the current supply circuit is advantageous because it accomplishes a reliable delivery of the control current with relatively simple means.

According to yet a preferred embodiment of this aspect of the invention, the at least one direct current supply circuit includes a high-input impedance buffer unit, which is adapted to receive a primary voltage signal from the electric sensor arrangement. In response thereto, the buffer unit generates a buffered voltage signal which reflects the voltage at the sensor electrodes. Naturally, an important function of the buffer unit is to prevent the control current from being fed back via the direct current supply circuit.

According to another preferred embodiment of this aspect of the invention, the conduit section includes at least one reference electrode in addition to the first and second sensor electrodes. This at least one reference electrode is adapted to produce a reference potential in the flowing fluid to which the voltage that is registered at the sensor electrodes is related. Either the at least one reference electrode applies a particular voltage, such as a ground voltage to the flowing fluid, or instead, the at least one reference electrode is used to register an externally applied voltage. In any case, the at least one reference electrode alleviates an accurate registration also of very small voltages between the sensor electrodes, which of course, is desirable feature.

According to still another preferred embodiment of this aspect of the invention, a fluid contact surface of at least one of the sensor electrodes contains platinum, for instance by being at least partly covered with platinum black. An important advantage is namely attained with this material, since it has an extremely large surface area. Thus, good electrical contact between the electrode and the fluid may be obtained via an electrode that has comparatively small dimensions.

According to another aspect of the invention, the object is achieved by the initially described ultra-filtration measuring unit, which is characterized in that it contains at least one flow sensor of the above-proposed type. Such an ultra-filtration measuring unit, for instance, enables reliable flow measurements in a dialysis apparatus where the dialysis liquid contains glucose. This is a highly desired characteristic in today's renal medicine.

According to a preferred embodiment of this aspect of the invention, the ultra-filtration measuring unit includes a measurement cell, wherein a first flow sensor is arranged with its conduit section in parallel with the conduit section of a second flow sensor, such that a common magnetic field may magnetize flowing fluid in both sensors. This design is advantageous because thereby, the circuitry for accomplishing the magnetization can be made relatively uncomplicated.

According to another aspect of the invention, the object is achieved by the initially described method for measuring a flow rate component, which is characterized by feeding at least one control current to an electric sensor arrangement for registering the voltage. The control current here has such sign and magnitude that a direct-current voltage level at the electric sensor arrangement is controlled towards a predetermined voltage, for example zero volt in relation to a reference potential.

As mentioned above, any DC-level drift which otherwise could have occurred due to an oxidation of one or more of the sensor electrodes is thereby prevented. At the same time, the flow measurement may be performed continuously, and/or flow rate sample values may be generated at an arbitrary interval. Both of these attributes are both highly desirable, particularly in medical applications.

According to a preferred embodiment of this aspect of the invention, the method includes the following steps. First, the registered voltage is compared with the predetermined voltage to produce a variance between the voltages. Then, a direct-current voltage component is extracted from this variance, which forms a basis for a control current. Finally, the control current is fed to the electric sensor arrangement, such that the direct-current voltage level at the electric sensor arrangement is controlled towards the predetermined voltage. It is generally preferable to complete these steps continuously and in parallel, such that for instance, during extraction of the DC-voltage from a particular variance, the variance between a somewhat later registered voltage and the predetermined voltage is determined, and so on.

According to yet a preferred embodiment of this aspect of the invention, the production of the control current involves the following sub-steps. First, an adjustment signal is received, which reflects the direct-current voltage component of the variance between the registered voltage and the predetermined voltage. Then, based on the adjustment signal, the control current is generated. Hence, an adaptive and straightforward regulation of the control current is accomplished.

According to another preferred embodiment of this aspect of the invention, the magnetic field has a base frequency which is different from a multiple of a typical electricity supply network frequency, such as 50 or 60 Hertz. Thereby, undesired resonance phenomena may namely be avoided.

Although the invention enhances the accuracy and reliability of flow measurements performed with respect to a fluid that risks interacting electrochemically with the sensor electrodes, the proposed solution is equally well suited for flow measurements of any non-corrosive fluids. The only requirement is that the fluid contains at least some amount of electrically charged elements.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED
EMBODIMENTS OF THE INVENTION

Figure 1:
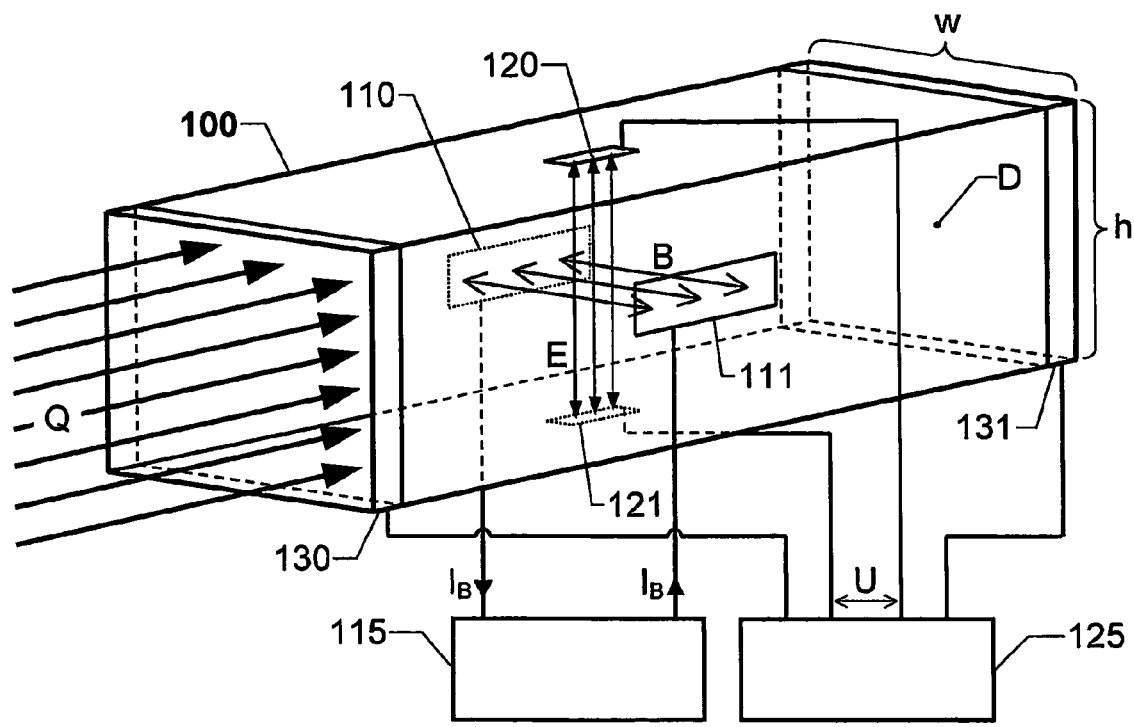
FIG. 1 shows a schematic view of a flow sensor according to the invention.

A schematic view of a flow sensor according to the invention is shown in FIG. 1. The sensor includes a conduit section 100 for receiving a fluid flow, a magnet driver 115 for controlling the polarity and intensity of a magnetic field B across the conduit section 100, and a voltage sensor 125 for registering a voltage U induced in the fluid flow by means of the magnetic field B.

The sensor measures a flow rate component Q along a selected direction of a fluid that flows through the conduit section 100. The selected direction (indicated with bold arrows) here coincides with longitudinal extension of the conduit section 100. The flow rate component Q is measured over the conduit section's 100 cross-section area D which, for illustrating purposes, in this example has a rectangular shape with a width w and a height h. In practice, however, any alternative cross-section shape is conceivable.

The fluid is presumed to contain electrically charged elements, such as ions. These elements are transported by the flowing fluid through the conduit section 100 at an average velocity v in the selected direction. A pair of controllable magnetizing means 110 and 111 respectively are arranged substantially opposite to each other in the conduit section 100, for example on the side walls. The magnetizing means 110 and 111 are oriented such that a magnetic axis between them is substantially perpendicular to the selected flow direction. Moreover, each magnetizing means 110 and 111 contains a conductor coil, which is electrically connected to the magnet driver 115. Thereby, by means of a magnetizing current $I_B$, the magnet driver 115 may generate a magnetic field B across the conduit section 100 between the magnetizing means 110; 111 whose intensity depends on the magnitude of the magnetizing current $I_B$, which is sent through the conductor coils. The polarity of this magnetic field B is determined by the sign (i.e. direction) of the magnetizing current $I_B$.

Figure 2A:
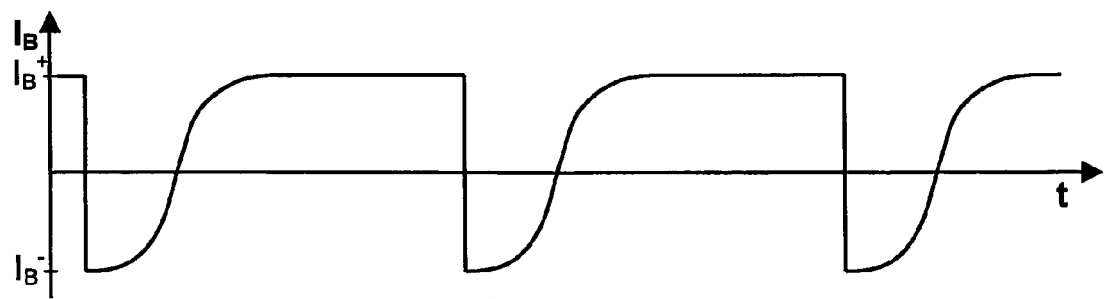
FIG. 2a shows a graph illustrating a magnetizing current which controls a magnetic field across a conduit section of the flow sensor according to an embodiment of the invention.

FIG. 2a shows an exemplary graph for such a magnetizing current $I_B$ for controlling the magnetic field B. Preferably, the current direction in the conductor coils of the magnetizing means 110 and 111 is reversed after each period of the magnetizing current $I_B$ (e.g. in connection with the negative edge from $I_B^+$ to $I_B^-$) by means of a switching operation, such that at the same time, the polarity of the magnetic field is altered. Due to the linear relationship between the magnetizing current $I_B$ and the magnetic field B, the graph in FIG. 2a could, in fact, also be regarded as an illustration of the intensity of the magnetic field B as a function of time t. However, it should be borne in mind that the current direction is reversed after completion of each magnetizing current period. Thus, one period of the magnetic field corresponds to two magnetizing current periods.

According to Faraday's law, an electric field E is produced in the flowing fluid as a result of an interaction between the electrically charged elements in the fluid and the magnetic field B. The electric field E has its maximum component in a direction, which is perpendicular to both the direction of the (largest) flow component and the axis of the magnetic field B, and may be expressed as E=v×B, where v represents the average velocity and B represents the magnetic field.

An electric sensor arrangement is used to register the electric field E by means of a first sensor electrode 120 and a second sensor electrode 121. The sensor electrodes 120 and 121 are arranged in the conduit section 100 to be wetted by the flowing fluid therein. According to a preferred embodiment of the invention, the fluid contact surface of the sensor electrodes 120 and 121 contains platinum, and more preferably, is at least partly covered with platinum black. Furthermore, in order to enable registration of a largest possible electrical field vector, the sensor electrodes 120 and 121 are spaced apart from one another along a line which is substantially perpendicular both to the selected flow direction and the magnetic axis of the magnetic field B. The voltage sensor 125 is electrically connected both to the first sensor electrode 120 and the second sensor electrode 121, so that the voltage sensor 125 may register a voltage U between the electrodes 120 and 121.

Figure 2B:
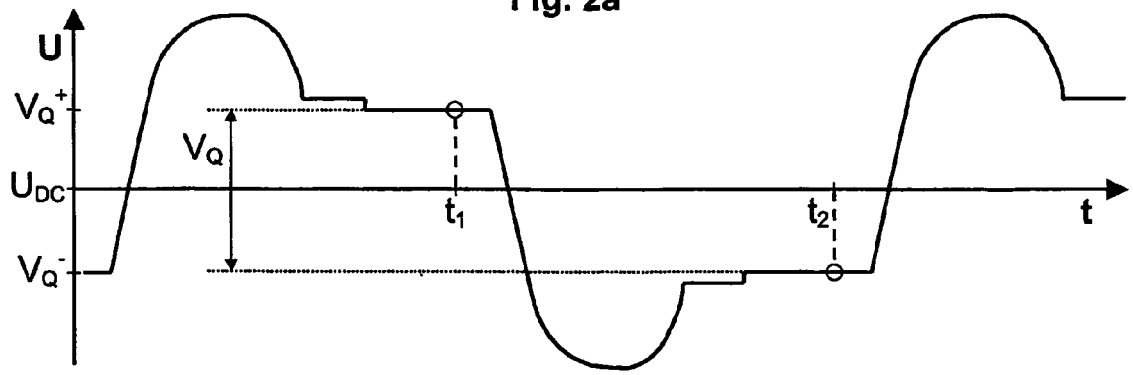
FIG. 2b shows a graph illustrating a corresponding electric field induced in the flowing fluid as a result of the magnetic field being produced by the magnetizing current illustrated in FIG. 2a, FIG. 3 depicts a block diagram over a proposed direct current supply circuit which feeds such a current to the sensor electrodes that their DC-voltage level is controlled towards a predetermined voltage.

Thus, in this example, where the sensor electrodes 120 and 121 are arranged on the floor and top walls of the conduit section 100, the distance between the sensor electrodes 120 and 121 is equal to the height h of the conduit section 100. Therefore, a voltage component $V_Q$ between the sensor electrodes 120 and 121 caused by the interaction between the electrically charged elements in the fluid and the magnetic field B may be expressed as: $V_Q$=v·B. The relationship between the flow rate component Q and the average velocity v is: Q=v·D·B, where D denotes the cross-section area of the conduit section 100. Consequently, the voltage component $V_Q$ may be expressed as $V_Q$=Q/D. The fact that the area D is constant renders the voltage component $V_Q$ proportional to the flow rate component Q. Moreover, it is generally preferable to measure the voltage U between the sensor electrodes 120 and 121 at time instances when the magnetic field has a particular (and substantially constant) value. FIG. 2b shows an exemplary graph which illustrates how a voltage component $V_Q$ may be defined based on measurements of the voltage U between the sensor electrodes 120 and 121.

According to a preferred embodiment of the invention, the conduit section 100 includes at least one reference electrode in addition to the first and second sensor electrodes 120 and 121. The flow sensor in FIG. 1 has two such reference electrodes 130 and 131, which both are adapted to produce a reference potential for the voltage U. Technically however, one reference electrode is sufficient. Typically, the reference voltage represents a ground potential applied to the flowing fluid in the conduit section 100 by means of the reference electrodes 130 and 131. However, any other electric potential is conceivable. According to an alternative embodiment of the invention, instead of applying a voltage, the reference electrodes 130 and 131 register an externally applied voltage to the fluid.

Since, preferably, the polarity of the magnetic field B varies regularly, for example in response to a magnetizing current $I_B$ according to the graph in FIG. 2a and a switching operation performed at the end of each period, the DC-component of the registered voltage U lacks interest for the flow measurement. Therefore, the DC-component should be suppressed. The reference electrodes 130 and 131 facilitate this suppression by supplying to the voltage sensor 125 an appropriate value of the DC-voltage level that is present in the flowing fluid, so that this component may be subtracted from the registered voltage U.

FIG. 2b shows a graph that illustrates an exemplary voltage U registered between the sensor electrodes 120 and 121 when the magnetizing current $I_B$ illustrated in FIG. 2a is fed to the magnetizing means 110 and 111, and a switching operation which alters the current direction is performed after completion of each period. In the illustrated example, the voltage signal U contains a DC-component $U_{DC}$, and as a result of said switching operation, two magnetizing current $I_B$ periods corresponds to one induced voltage U period.

In order to avoid the occurrence of undesired resonance phenomena, it is preferable to select the base frequency of the magnetic field B to a value being different from a multiple of a typical electrical supply network frequency (such as 50 Hz or 60 Hz). Consequently, 401 Hz constitutes one example of a suitable magnetic field frequency.

Preferably, the voltage signal U is sampled at time instances $t_1$ and $t_2$, when the signal has attained a stable value (e.g. corresponding to when the magnetizing current $I_B$ has reached a constant positive level $I_B^+$, shortly prior to switching over to a negative current value $I_B^-$). Due to the varying polarity of the magnetic field B, the voltage signal U also varies over time. A first relatively stable voltage level $V_Q^+$ and a second relatively stable voltage level $V_Q^-$ respectively (corresponding to the constant level $I_B^+$ of the magnetizing current $I_B$) may be registered at the sampling instances $t_1$, $t_2$ and so on. The voltage difference $V_Q$ between the voltage levels $V_Q^+$ and $V_Q^-$ here constitutes a measure of the flow rate Q of the fluid flowing through the conduit section 100.

Figure 3:
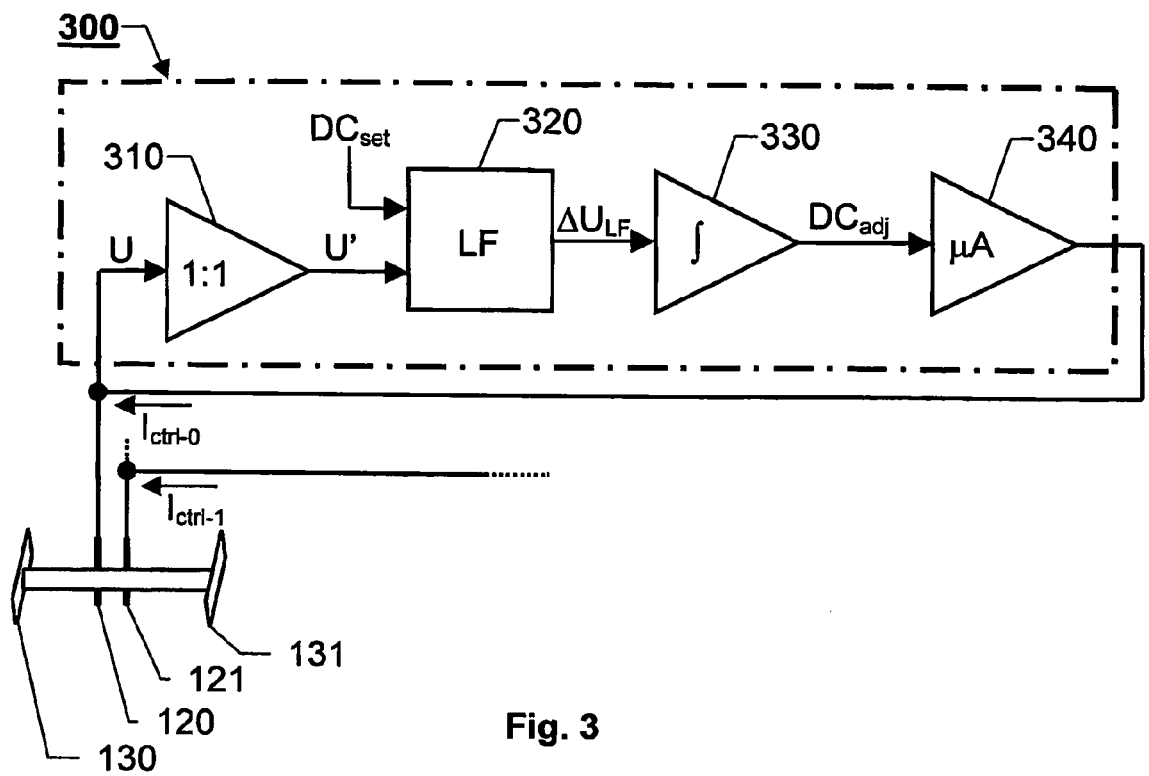

According to the invention, the flow sensor also includes at least one direct current supply circuit 300, which is adapted to feed a control current $I_{ctrl-0}$ to the electric sensor arrangement (i.e. each of the first and the second sensor electrodes 120 and 121) of such sign and magnitude that the DC voltage level at the sensor electrodes 120 and 121 relative a reference potential (e.g. produced by the reference electrodes 130 and 131) is controlled towards a predetermined voltage, say zero volts. FIG. 3 depicts a block diagram over a proposed direct current supply circuit for supplying a control current $I_{ctrl-0}$ to the first sensor electrode 120. An equivalent direct current supply circuit is also used to produce a corresponding control current $I_{ctrl-1}$ to the second sensor electrode 121, however for reasons of simplicity, this circuit is not explicitly depicted in the figure.

The direct current supply circuit 300 includes a differential low-pass filtering unit 320, an integrator unit 330 and a controllable current generator 340. Preferably, the direct current supply circuit 300 also includes a high-input impedance buffer unit 310, which is adapted to receive a primary voltage signal U from the electric sensor arrangement, and in response thereto, generate a buffered voltage signal U' reflecting the voltage at the first sensor electrode 120 and the second sensor electrode 121. The differential low-pass filtering unit 320 receives the registered voltage U (either directly from the electric sensor arrangement, or via the buffer unit 310), receives a predetermined voltage $DC_{set}$ (typically generated on basis of values at the reference electrodes 130 and 131), and extracts there from a low-pass filtered difference signal $\Delta U_{LF}$ representing a DC-difference value between the predetermined voltage $DC_{set}$ and the registered voltage signal U (or U'). The integrator unit 330 is adapted to receive the low-pass filtered difference signal $\Delta U_{LF}$, and in response thereto, produce an adjustment signal $DC_{adj}$, which represents a measure of how much the DC-voltage level at the electric sensor arrangement should be adjusted in order to reach the desired voltage $DC_{set}$. Thus, the differential low-pass filtering unit 320 and the integrator unit 330 together form the PI-part of a PI-regulator for the DC-voltage at the electric sensor arrangement.

The controllable current generator 340 is adapted to receive the adjustment signal $DC_{adj}$, and in response thereto, produce the control current $I_{ctrl-0}$, which is fed to the first sensor electrode 120 in the electric sensor arrangement. Analogous thereto, a corresponding control current $I_{ctrl-1}$ is fed to the second sensor electrode 121. Thereby, the DC-voltage level at the sensor electrodes 120 and 121 is controlled towards the predetermined voltage.

Figure 4:
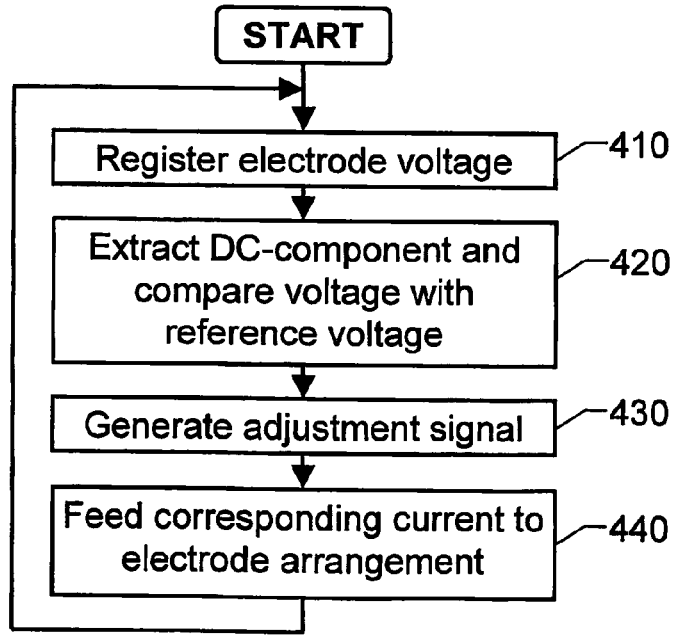
FIG. 4 shows a flow diagram which illustrates the general method according to the invention.

FIG. 4 shows a flow diagram illustrating the general method according to the invention for measuring a flow rate component of a fluid, which contains electrically charged elements.

The method presupposes that the fluid is magnetized by means of a magnetic field B having a periodically alternating polarity and a magnetic axis which is oriented substantially perpendicular to a selected flow direction along which the flow rate is to be measured. Moreover, a voltage is registered across the flowing fluid along a line being substantially perpendicular both to the selected flow direction and the magnetic axis.

A first step of the method 410, registers a sensor electrode voltage. Then, a step 420 extracts a DC-voltage component from the registered voltage and compares the DC-voltage component with a predetermined voltage that represents a reference value with respect to the DC-voltage level of the flow sensor. Subsequently, a step 430 generates an adjustment signal, which in turn forms a basis for producing a control current. After that, a step 440 feeds this control current to the sensor electrodes. The control current has such sign and magnitude that the direct-current voltage level at the sensor electrodes is controlled towards the predetermined voltage.

Figure 5:
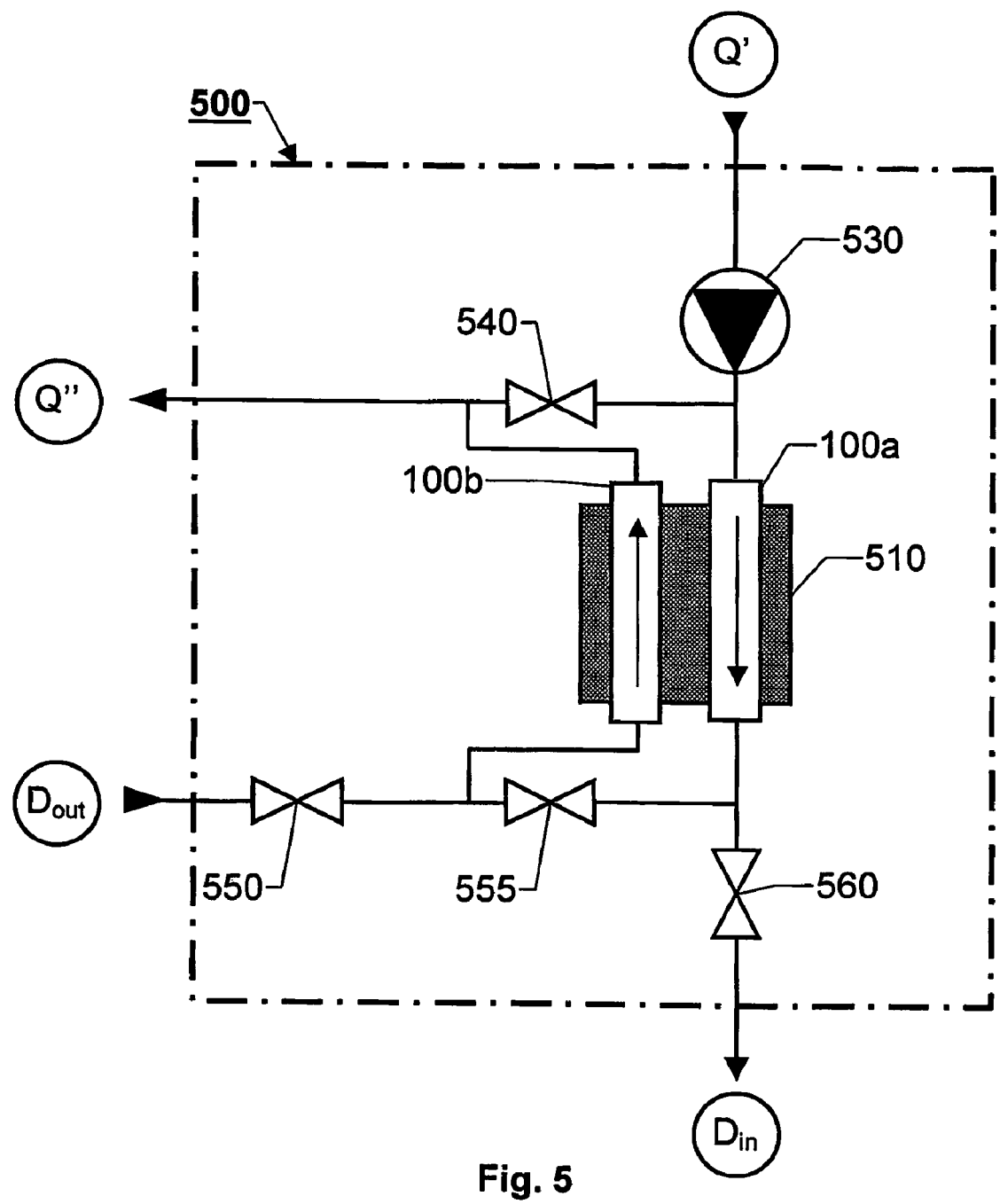
FIG. 5 shows a schematic view of an ultra-filtration measuring unit according to an embodiment of the invention.

FIG. 5 shows a schematic view of an ultra-filtration measuring unit 500 according to an embodiment of the invention. The unit 500 may be used to regulate the flows of dialysis liquid (e.g. containing glucose) to and from a dialysis apparatus.

The proposed ultra-filtration measuring unit 500 includes a pump 530, a measurement cell 510, and valves 540, 550, 555 and 560. The pump 530 assists in accomplishing a desired flow Q' of uncontaminated dialysis liquid to the dialysis apparatus $D_{in}$. The valves 540, 550, 555 and 560 are used to control the ultra-filtration volume per time unit. An output flow $D_{out}$ of used dialysis liquid from the dialysis apparatus is received by the unit 500 via the valve 550, and fed out for discarding Q" via the measurement cell 510.

The measurement cell 510 contains a first flow sensor 100a located in a first flow channel and a second flow sensor 100b located in a second flow channel. The flow sensors 100a and 100b are arranged with their conduit sections in parallel with each other, such that a common magnetic field may magnetize flowing fluid in both the first flow sensor 100a and the second flow sensor 100b. This design is namely advantageous because thereby, the circuitry for accomplishing the magnetization can be made relatively uncomplicated. The measurement cell 510 measures the flow rate of dialysis liquid into the dialysis apparatus $D_{in}$ via the first flow channel, and a corresponding flow rate $D_{out}$ from the dialysis apparatus via the second flow channel. Thus, by measurements performed in the measurement cell 510, the flow rates $D_{in}(Q')$ and $D_{out}(Q")$ can be controlled to obtain a desired ultra-filtration volume per time unit.

In order to prevent (or at least minimize) calculation errors in the flow measurements, the measuring unit 500 performs self-calibration, by means of a so-called taration procedure, at regular intervals (typically once every 30 minutes during the dialysis treatment).

The taration procedure includes one phase in which a zero-flow is measured. Here, the valve 540 is open and the valves 550, 555 and 560 are closed, so that the flow Q' of uncontaminated dialysis liquid is fed out directly for discarding Q" without passing the measurement cell 510 or the dialysis apparatus.

In another phase of the taration procedure, a differential flow between the two flow channels is measured and set to zero. Here, the valve 555 is open while the valves 540, 550 and 560 are closed, so that the flow Q' of uncontaminated dialysis liquid passes the measurement cell 510 via both the first and the second flow channels, and is then fed out for discarding Q" (i.e. without passing the dialysis apparatus). Preferably, in this phase, the flow Q' is set to a standardized and well-defined value, say 500 ml/minute.

Based on the above zero-flow- and differential-flow-measurements any adjustments necessary to the flow rate calculations performed on the values delivered by the measurement cell 510 can be made, so that systematic future calculation errors are avoided.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A flow sensor for measuring a flow rate component of a fluid containing electrically charged elements, in a selected direction the flow sensor, comprising:
   a conduit section for transporting the fluid;
   first and second controllable magnetizing devices arranged substantially opposite to each other in the conduit section wherein a magnetic axis between said first and second magnetizing devices is substantially perpendicular to the selected flow direction of the fluid in the conduit section;
   a magnet driver configured to control a polarity of a magnetic field between the first and the second magnetizing devices;
   an electric sensor arrangement including first and second sensor electrodes provided in the conduit section, the first and second sensor electrodes configured to be wetted by the fluid, the first and second sensor electrodes being spaced apart from one another along a line substantially perpendicular to both the selected flow direction and the magnetic axis; and
   a voltage sensor configured to register a voltage between the first sensor electrode and the second sensor electrode wherein the flow sensor comprises a direct current supply circuit configured to feed first and second control currents ($I_{ctrl-0}$; $I_{ctrl-1}$) to each of the first and second sensor electrodes in the electric sensor arrangement, said first and second control currents ($I_{ctrl-0}$; $I_{ctrl-1}$) each having a sign and a magnitude, wherein said sign and said magnitude cause a direct-current voltage level at the first and second sensor electrodes relative to a reference potential to be controlled toward a predetermined voltage ($DC_{set}$).

2. A flow sensor according to claim 1, wherein the direct supply circuit comprises:
   a differential low-pass filtering unit configured to generate a low-pass filtered difference signal ($\Delta U_{LF}$) representing a variance between the predetermined voltage ($DC_{set}$) and the registered voltage;
   an integrator unit configured to produce an adjustment signal ($DC_{adj}$) in response to receiving the low-pass filtered difference signal ($\Delta U_{LF}$); and
   a controllable current generator configured to produce the first control current ($I_{ctrl-0}$) in response to the adjustment signal ($DC_{adj}$).

3. A flow sensor according to claim 2, wherein the direct current supply circuit comprises a buffer unit configured to receive a primary voltage signal from the electric sensor arrangement and to generate a buffered voltage signal reflecting a voltage at the first sensor electrode and second sensor electrode in response to said primary voltage signal, wherein an input of the buffer unit for receiving the primary voltage signal has a relatively high impedance.

4. A flow sensor according to claim 1, wherein the conduit section comprises at least one reference electrode the at least one reference electrode being configured to produce a reference potential for registering the voltage between the first and second sensor electrodes.

5. A flow sensor according to claim 1, wherein the fluid contains glucose.

6. A flow sensor according to claim 1, wherein a fluid contact surface on at least one of the first and second sensor electrodes includes platinum.

7. A flow sensor according to claim 6, wherein the fluid contact surface on at least one of the first and second sensor electrodes is at least partially covered with platinum black.

8. An ultra-filtration measuring unit for regulating at least one dialysis flow, comprising at least one flow sensor according to claim 1.

9. An ultra-filtration measuring unit according to claim 8 further comprising a measurement cell and first and second flow sensors having conduit sections, the conduit section of said first flow sensor being configured parallel to the conduit section of said second flow sensor, wherein a common magnetic field is configured to magnetize fluid flowing in both the first flow sensor and the second flow sensor.

10. A method for measuring a flow rate component of a fluid including electrically charged elements in a selected direction, the method comprising the steps of:
    magnetizing the fluid by means of a magnetic field having a periodically alternating polarity having a magnetic axis which is oriented substantially perpendicular to the selected direction;
    feeding at least one control current to an electric sensor arrangement for registering the voltage the at least one control current having a sign and a magnitude, wherein said sign and said magnitude cause a direct-current voltage level at the electric sensor arrangement to be controlled towards a predetermined voltage ($DC_{set}$) relative to a reference potential; and
    registering a voltage across the fluid along a line substantially perpendicular to both the selected direction and the magnetic axis.

11. A method according to claim 10, further comprising the steps of:
    comparing the registered voltage with the predetermined voltage ($DC_{set}$) to produce a variance;
    extracting a differential direct-current voltage component ($\Delta U_{LF}$) from the variance;
    producing a control current in response to the differential direct-current voltage component ($\Delta U_{LF}$); and
    feeding the control current to the electric sensor arrangement.

12. A method according to claim 11, wherein the step of producing the control current further comprises the sub-steps of:
    receiving an adjustment signal ($DC_{adj}$) reflecting the differential direct-current voltage component ($\Delta U_{LF}$) of the variance; and
    generating the control current based on the adjustment signal ($DC_{adj}$).

13. A method according to claim 10 wherein the magnetic field has a base frequency different from a multiple of a standardized electricity supply network frequency.

14. A method according to any one of the claims 10-13, wherein the fluid includes glucose.

* * * * *

UNITED STATES PATENT AND TRADEMARK OFFICE
CERTIFICATE OF CORRECTION

| | |
|---|---|
| PATENT NO. | : 7,246,530 B2 |
| APPLICATION NO. | : 10/544671 |
| DATED | : July 24, 2007 |
| INVENTOR(S) | : Hallstadius et al. |

Page 1 of 1

It is certified that error appears in the above-identified patent and that said Letters Patent is hereby corrected as shown below:

On the title page, item (57), line 15, "areference" should read --a reference--.

On the title page, item (57), line 15, "controled" should read --controlled--.

Signed and Sealed this

Sixteenth Day of October, 2007

JON W. DUDAS
*Director of the United States Patent and Trademark Office*